United States Patent
Phan et al.

(10) Patent No.: US 6,724,476 B1
(45) Date of Patent: Apr. 20, 2004

(54) LOW DEFECT METROLOGY APPROACH ON CLEAN TRACK USING INTEGRATED METROLOGY

(75) Inventors: Khoi A. Phan, San Jose, CA (US); Bhanwar Singh, Morgan Hill, CA (US); Bharath Rangarajan, Santa Clara, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 10/261,756

(22) Filed: Oct. 1, 2002

(51) Int. Cl.$^7$ .............................................. G01N 21/00
(52) U.S. Cl. ................. 356/237.4; 356/237.3; 356/237.5
(58) Field of Search .................... 356/237.3, 237.4, 356/237.5; 438/16; 250/559.41, 559.42, 559.45

(56) References Cited

U.S. PATENT DOCUMENTS

| | | | | |
|---|---|---|---|---|
| 4,247,203 A | * | 1/1981 | Levy et al. ................. | 356/398 |
| 4,376,583 A | * | 3/1983 | Alford et al. ............ | 356/237.2 |
| 5,537,325 A | * | 7/1996 | Iwakiri et al. ....... | 257/E23.179 |
| 5,801,965 A | * | 9/1998 | Takagi et al. ............. | 356/237.1 |
| 5,900,633 A | * | 5/1999 | Solomon et al. ............... | 356/73 |
| 6,016,562 A | * | 1/2000 | Miyazaki et al. ......... | 356/237.1 |
| 6,172,365 B1 | * | 1/2001 | Hiroi et al. .................. | 250/310 |
| 6,204,917 B1 | * | 3/2001 | Smedt ...................... | 356/237.5 |
| 6,263,099 B1 | * | 7/2001 | Maeda et al. ............... | 356/394 |
| 6,624,078 B1 | * | 9/2003 | Ravkin ....................... | 438/692 |
| 6,633,831 B2 | * | 10/2003 | Nikoonahad et al. ....... | 702/155 |

\* cited by examiner

*Primary Examiner*—Michael P. Stafira
*Assistant Examiner*—Juan D Valentin, II
(74) *Attorney, Agent, or Firm*—Amin & Turocy, LLP

(57) ABSTRACT

One aspect of the present invention relates to a system and method of monitoring for defects on a wafer before and after forming a photoresist layer on the wafer. The system includes a device fabrication system comprising one or more wafer processing system components for producing a device; a defect metrology system integrated within and on track with the fabrication system operative to inspect the wafer for defects before it proceeds to photoresist processing; and a wafer cleaning system for reducing an amount of defects detected on the front and/or back side of the wafer. If the amount of defects have been sufficiently reduced, the front side of the wafer may be coated with a photoresist. Subsequently, the back side of the wafer may be inspected and cleaned while protecting the front side from damage. Cleaning of the wafer may be performed with a thermal shock treatment, for example.

21 Claims, 4 Drawing Sheets

LOW DEFECT METROLOGY APPROACH ON CLEAN TRACK USING INTEGRATED METROLOGY

TECHNICAL FIELD

The present invention generally relates to processing a semiconductor substrate. In particular, the present invention relates to monitoring and measuring a wafer for defects prior to subjecting the wafer to resist processing in order to determine the source of such defects and to remove such defects prior to resist processing.

BACKGROUND ART

Achieving the objectives of miniaturization and higher packing densities continue to drive the semiconductor manufacturing industry toward improving semiconductor processing in every aspect of the fabrication process. Several factors and variables are involved in the fabrication process. For example, at least one and typically more than one photolithography process may be employed during the fabrication of a semiconductor device. Each factor and variable implemented during fabrication must be considered and improved in order to achieve the higher packing densities and smaller, more precisely formed semiconductor structures.

In general, lithography refers to processes for pattern transfer between various media. It is a technique used for integrated circuit fabrication in which a silicon slice, the wafer, is coated uniformly with a radiation-sensitive film, the photoresist, and an exposing source (such as optical light, X-rays, or an electron beam) illuminates selected areas of the surface through an intervening master template, the photoresist mask, for a particular pattern. The lithographic coating is generally a radiation-sensitized coating suitable for receiving a projected image of the subject pattern. Once the image is projected, it is indelibly formed in the coating. The projected image may be either a negative or a positive of the subject pattern. Exposure of the coating through the photoresist mask causes a chemical transformation in the exposed areas of the coating thereby making the image area either more or less soluble (depending on the coating) in a particular solvent developer. The more soluble areas are removed in the developing process to leave the pattern image in the coating as less soluble polymer. The resulting pattern image in the coating, or layer, may be at least one portion of a semiconductor device that contributes to the overall structure and function of the device.

Defects on the semiconductor device can occur at random as well as multiple locations on the device and at various stages while manufacturing the device. However, some defects are more problematic than others. For example, defects on the wafer which occur before depositing a photoresist on the wafer can linger and cause problems in subsequent processing (e.g., patterning the photoresist and processes using the malformed patterned photoresist such as an etch process and the like). Thus defects present at the start of resist processing (e.g., photolithography) tend to propagate themselves through subsequent processing. Furthermore, defects may also form on the wafer during wafer transfer from process to process.

Conventional defect detection systems which utilize wafer clean tools and endpoint detection techniques have been useful in cleaning the wafer before processing and detecting defects on the completed semiconductor device. However, defects can arise on the wafer while transferring it from the off-line wafer clean tools to the processing stage. In addition, end-point systems examine the completed or substantially completed device such that some defects may be undetectable. As can be seen, either defect detection system is unable to determine the source of the defect and/or remove the defects effectively. Defects may render the device partially or entirely inoperable. As a result, the wafer would need to be reworked or repaired in order remove such defects. Furthermore, since detection methods currently in use are incapable of distinguishing between sources of defects, the same or similar defects will arise again in future devices fabricated under similar process conditions. Overall, costs and product waste increase while production efficiency decreases due to conventional defect detection techniques.

Accordingly, there is an unmet need for an effective defect detection and cleaning system that leads to increased product yields and decreased product costs and waste.

SUMMARY OF THE INVENTION

The present invention provides a system and method for integrated defect metrology and defect removal. More specifically, the present invention provides an on-line track system and method for monitoring a front and back side of a wafer for defects before and after a resist coat, cleaning a front and backside of a wafer using effective cleaning tools, and distinguishing between defects introduced before and after a resist coat process. According to one aspect of the present invention, the system and method involve on-track defect detection about the front and back sides of the wafer prior to a photoresist coating lithography process in order to distinguish between defects caused by wafer preparation and defects caused by resist processing.

This is accomplished in part by providing a track system having built-in particle defect monitor as well as a clean system. In particular, a wafer is placed on a track and directed to pass through an integrated defect metrology system before being subjected to any resist processing. The defect metrology system provides a pre-resist coat inspection of the front and back sides of the wafer for defects. Upon the detection of such, the defects can be measured and such measurements can be translated into a value or set of values understandable to a user by an analyzing system. In order to determine whether such defects (or level of defects) satisfies the acceptable defect limits, a comparison may be performed between the measured values and the accepted limits.

When measured defects exceed the acceptable defect limits or reach a range which is unacceptable by wafer standards, the wafer may be automatically routed to a wafer clean system. Using various water rinse techniques, the wafer clean system may reduce the amount of defects on the front and/or back sides of the wafer in preparation of the resist coat process. After the wafer is cleaned, it returns for a subsequent pre-resist coat inspection. When the wafer is determined to be substantially "clean", the wafer may proceed to a resist processing phase in order to receive a photoresist layer thereon and to continue with the fabrication process.

Following resist processing on the wafer, the front and back sides of the wafer can be inspected again to determine whether defects have accumulated on either side of the wafer such as for example during holding or transferring periods.

Alternatively, or in addition, some wafers can be discarded when their quantity of defects are beyond a cleanable or repairable range. This range may be determined by a user or by the type of device being made.

One aspect of the present invention relates to a system for a system for on-track monitoring of defects on a wafer before subjecting the water to resist processing. The system includes a device fabrication system comprising a photoresist coating system and at least one or more wafer processing components for producing a device from a wafer structure; a defect metrology system integrated with the device fabrication system operative to inspect at least one of a front side and a back side of the wafer structure for defects and to provide defect information about the wafer structure before it proceeds to the photoresist coating system; and a water cleaning system comprising at least one of a pre-resist coat cleaning module and a post-resist coat cleaning module, the system being operatively connected to the defect metrology system for reducing an amount of defects detected on the wafer structure such that after the amount of defects detected thereon are reduced, the wafer structure proceeds to the photoresist coating system component.

Another aspect of the present invention relates to a method for on-track monitoring of defects on a wafer before subjecting the wafer to resist processing. The method involves introducing a pre-resist coat wafer structure into a device fabrication system in order to yield a device product, the wafer structure having a front side and back side; monitoring at least one of the front side and the back side of the wafer structure for defects before a photoresist layer is formed on the wafer structure; measuring the defects found on the wafer structure in order to obtain defect information relating to the defects found on the wafer structure; comparing the defect information with threshold defect limits; and cleaning at least one of the front side and the back side of the wafer structure to reduce the defects found on that side of the wafer structure prior to forming a photoresist layer over the front side of the wafer structure.

Yet another aspect of the present invention relates to a An on-line method for real-time pre-resist coat and post-resist coat inspection of a wafer for defects. The method involves providing a pre-resist coat wafer structure, the wafer structure having a front side surface and a back side surface; inspecting at least one of the front side surface and the back side surface of the pre-resist coat water structure for defects; measuring the defects found on the pre-resist coat water structure in order to obtain defect information relating to the defects found on the wafer structure; cleaning at least one of the front side and the back side of the wafer structure to reduce the defects found on that side of the pre-resist coat wafer structure when the measured defects on that side are greater than the threshold defect limits; forming a photoresist layer over the front side of the pre-resist coat wafer structure to create a resist-coated wafer structure; inspecting the back side of the resist-coated wafer structure for defects without adversely affecting the front side of the resist-coated wafer structure; cleaning the beck side of the resist-coated wafer structure to remove any defects found thereon; and patterning the resist-coated wafer structure to thereby form one or more features in the wafer structure.

DISCLOSURE OF INVENTION

Figure 1:
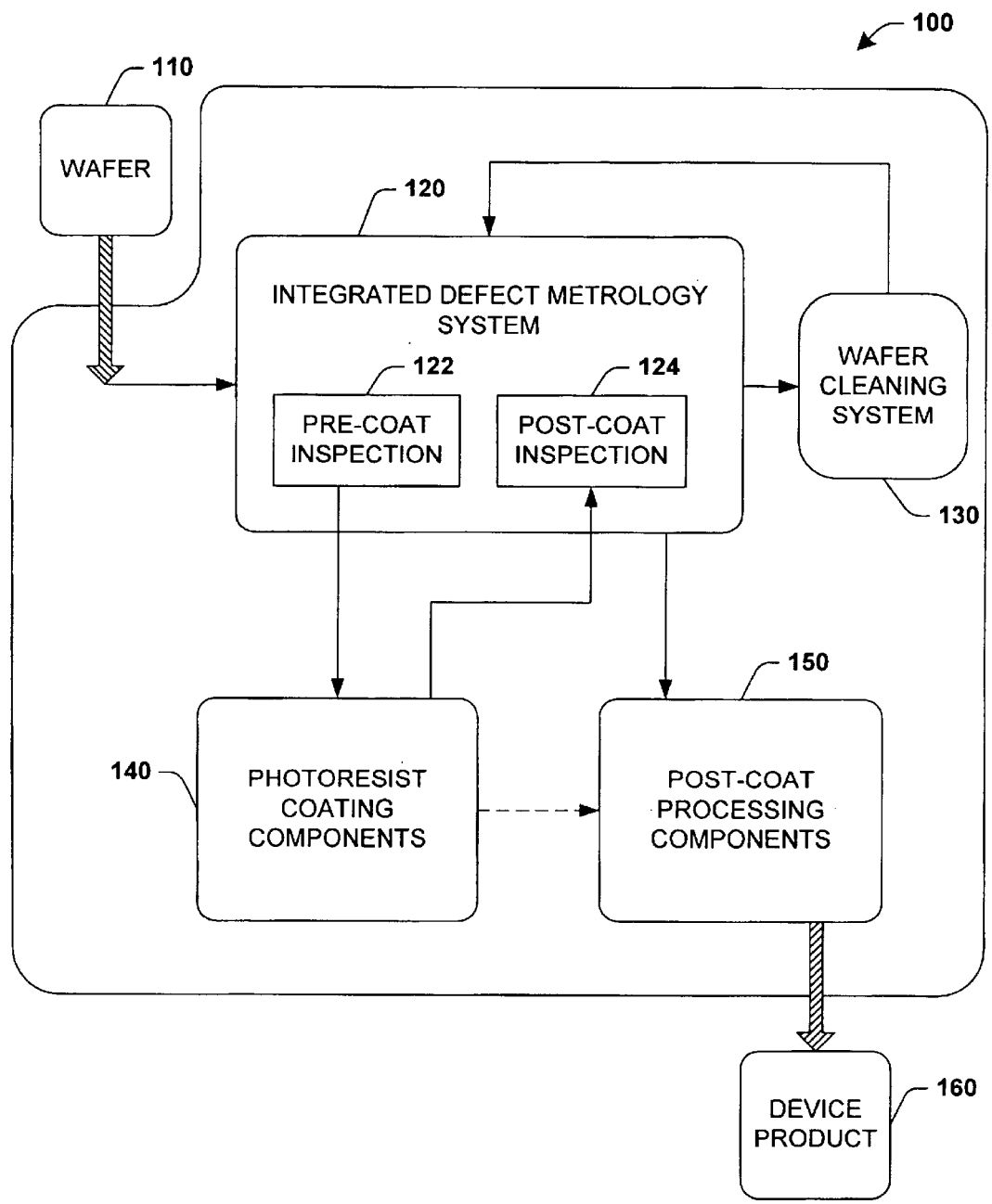
FIG. 1 illustrates a high-level, schematic block diagram of a system for detecting defects on a wafer structure prior to resist processing in accordance with an aspect of the present invention.

The present invention involves an on-line system and method for inspecting a wafer for particle defects before and after a resist coat process. More specifically, the present invention provides a system and method for monitoring particle defect formation on a front and back side of the wafer to determine either to clean the wafer or to allow the wafer to proceed to further resist lithography steps. Because defects present prior to and/or after resist processing tend to propagate themselves through the subsequent processing of the wafer, inspection for particle defects at these stages is critical to the performance of the wafer.

Removing the wafer from the fabrication track in order to clean the wafer as is done conventionally may not remove substantially all or enough of the defects since additional defects may accumulate during periods of transfer between the off-line clean system and the online fabrication system. Thus, the present invention provides an on-track defect metrology inspection and clean system and method for the same which reduces and/or eliminates the defects more effectively and efficiently to mitigate further deficiencies from occurring later and throughout the fabrication process.

This may be accomplished in part by using an integrated defect metrology system to measure the defects detected on or about the front and back sides of the wafer structure and then to transform the measurements into a value or set of values which may be used for comparison and/or analysis with respect to accepted defect limits. For example, the measured values are compared to values relating to a tolerable level of defects on the wafer structure. The tolerable levels depend on the type of device being manufactured and the type of application for which the device is to be used. Measurements of the wafer may be obtained by employing scatterometry, spectroscopic reflectometry, and/or fluorescent techniques where particle detection sensitivity of 10 microns and above may be sufficient.

The wafer structure may be subjected to a pre-resist coat and a post-resist coat inspection. In particular, the pre-coat inspection facilitates determining whether the wafer surfaces (e.g., front and back sides) are clean enough to receive the resist coating. The wafer is held in place over and by a chuck. Particles settling on the back side of the wafer may obscure or inhibit proper focusing from the back side of the wafer by the chuck during resist processing (e.g., photolithography). The post-coat inspection provides an additional level of particle defect detection to mitigate particle defects from settling on to the wafer surfaces during transfer between process steps.

According to one aspect of the present invention, a wafer clean system is located on the Fabrication track system. That is, when a wafer needs to be cleaned prior to resist coating, it can he routed along the track to the clean system rather than being taken off-line via an automated process controller (APC). Thus, a closed loop system results between the defect metrology system and the wafer clean system, both of which are maintained within the fabrication system.

The wafer clean system may provide any number of separate cleaning techniques. For example, if a defect metrology system finds that a particle count on a wafer surface (front and/or back side) is higher than desired prior to resist coating, the front and/or back side surfaces can be cleaned by using a thermal shock treatment. The thermal shock treatment involves two separate water lines, each supplying either hot or cold deionized (DI) water to the wafer surface. The wafer surface is washed with hot water for a tune period and then immediately rinsed with cold water. The thermal shock treatment facilitates removal of the particle defects from the targeted surface. In order to further increase particle removal, the cold DI water rinse may be via a programmable moving nozzle or arm such that the moving arm may contact a substantial amount of the targeted surface. In addition, the programmable aspect permits a user to isolate areas on the wafer surface for cleaning. The nozzle may include an interchangeable spray (circular) or stream (slit) opening through which the DI water is released onto the surface.

When cleaning the back side surface of the wafer before the resist coating, scrubbing may also be applied in addition to the DI water thermal shock treatment. In particular, the DI water can be delivered in a megasonic mode. The megasonic mode provides a soundwave (vibration) which can move through liquid in order to facilitate removal of particles from (he backside surface. The megasonic mode may only be employed for backside cleaning since there is substantially no damage potential to the back side of the wafer as compared to the front side.

Following the resist coat of the front side surface of the wafer, the back side of the wafer may be inspected for particle defects without substantially or adversely affecting the front side surface. This may be accomplished in part by rotating the wafer such that it is held by its edges. With the front or resist-coated side of the wafer blanketed by nitrogen ($N_2$) gas, the back side surface of the water may be subjected to a thermal shock cleaning treatment where the DI water may be supplied in megasonic mode if desired. The post-coat inspection and cleaning may remove any particles which might have settled onto the back side of the wafer during transference or transitions between chambers and the like.

According to another aspect of the present invention, an artificial intelligence system may be employed in order to determine which wafers require a cleaning. Thus, not every wafer is cleaned. Rather, only the wafers which fail to meet a threshold specification (particle defect) limit are cleaned in the manners described above.

In addition, the present invention facilitates distinguishing between defects introduced on the wafer structure during preparation of the wafer and defects introduced on the wafer during subsequent processing stages. For example, photoresist deposition and subsequent processing may cause defects on the wafer structure. However, as the fabrication progresses through various processing stages, the sources or origins of defects detected on the device may be indiscernible. The system and method of the present invention facilitate separating defects arising during preparation of the wafer structure from defects introduced later as a result of a photoresist processing step (phase). This permits the user to determine a source and/or cause of the defects detected as well as to implement modifications to the system and method for producing the device in order to mitigate future defect formation. Such modifications may be implemented using control feedback and/or feed forward mechanisms. As a result, the present invention increases fabrication efficiencies and fewer resources are consumed to re-work or repair defect-ridden device products.

The present invention will now be described in FIGS. 1–4 below with respect to a wafer structure entering a device fabrication system to transform the wafer structure into a device product. The device fabrication system may be programmed to produce a device product from the wafer structure using any number of processes as well as processing components which are necessary to properly manufacture the device.

FIG. 1 illustrates a high-level, schematic block diagram of a system 100 for monitoring defect formation on a wafer structure 110 prior to further processing by a device fabrication system. The system 100 includes a defect metrology system 120 which may be integrated into the device fabrication system such that the defect metrology system 120 is situated along a track or fabrication assembly line within the device fabrication system. Thus, the wafer structure 110 can be directed to pass through the defect metrology system 120 as the wafer structure 110 proceeds along the fabrication line.

The defect metrology system 120 may inspect the water structure for particle defects at any time before the wafer structure 110 is coated with a photoresist layer. For example, the wafer structure 110 may be subjected to a pre-coat inspection 122. Any defects detected while the wafer structure is at this stage of the device fabrication system can be isolated from other defects which might arise from subsequent processing stages. In addition, the wafer structure may also be cleaned to reduce and/or remove the defects from the wafer structure. This early detection and removal facilitates obtaining a defect-free device product.

The system 100 also includes a wafer cleaning system 130, which is operatively connected to the defect metrology system 120. When activated, the wafer cleaning system 130 may reduce an amount of defects detected on the wafer structure 110 by employing a cleaning process suitable to remove such defects. The wafer cleaning system 130 can be activated by the defect metrology system 120 to receive the wafer structure for cleaning. Once the wafer structure 110 is substantially cleaned, the wafer cleaning system 130 transfers the wafer structure 110 back to the defect metrology system 120 for monitoring to locate defects which may still be present on the wafer structure 110. In addition, the defect metrology system can determine whether the amount of defects still remaining on the wafer structure 110 is acceptable for the wafer structure 110 to continue through the device fabrication system.

When it has been determined that the wafer structure 110 may proceed, the defect metrology system 120 moves the wafer structure 110 to a photoresist coating component 140. The photoresist coating component 140 can form a photoresist layer onto the wafer structure 110. Because particle defects can form on the wafer, and the back side of the water, in particular, the resist coated wafer structure 110 can be transferred back to integrated defect metrology system 120 in order to undergo a post-coat inspection 124. Subsequently, the resist-coated wafer structure 110 moves through the fabrication system to further post-coat processing components 150 in order to completely form a device product 160. Alternatively, the resist-coated wafer structure may be routed directly to the post-coat processing components 150.

Figure 2:
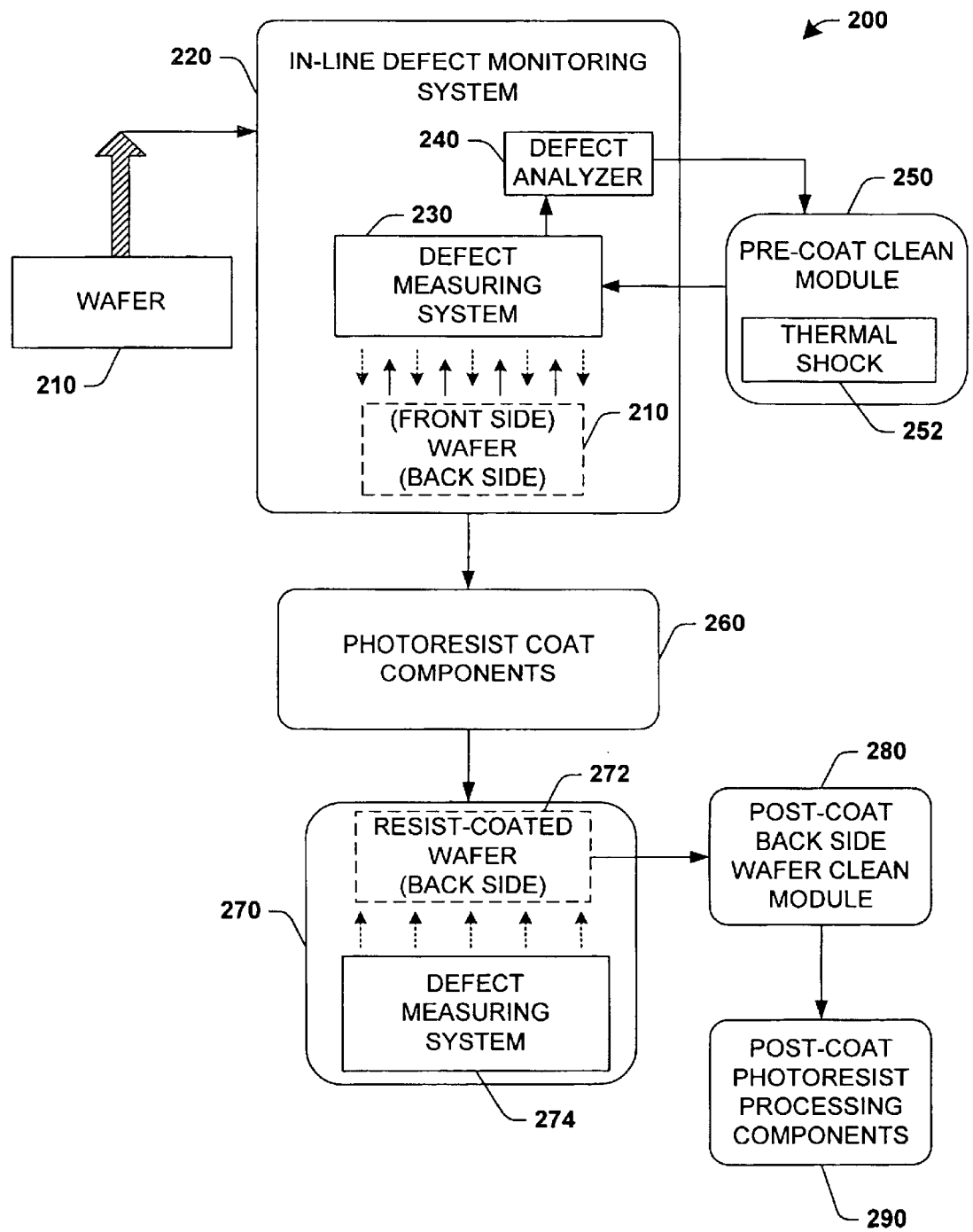
FIG. 2 illustrates a schematic block diagram of a system for detecting defects on a wafer structure prior to forming and processing a photoresist on the wafer in accordance with an aspect of the present invention.

In accordance with another aspect of the present invention, FIG. 2 demonstrates a schematic block diagram of a device fabrication system 200 for reducing particle defects on pre-resist and post-resist coated wafers. The device fabrication system 200 comprises at least one or more wafer processing components and a photoresist processing system which is to be described in further detail below. These wafer processing components may be implemented early and/or throughout the device fabrication process. It should be understood and appreciated that the wafer processing components may be employed for the current wafer as well as for future wafers and such is intended to fall within the scope of the present invention.

The system 200 involves a wafer 210 which has been prepared to undergo a fabrication process. In particular, the wafer 210 is to be subjected to various processing steps within the fabrication process in order to yield a device product. The system includes an in-line defect monitoring system 220 for examining the wafer 210 for particle defects. According to one aspect of the present invention, the wafer 210 can be monitored for the defects before and after it is coated with a photoresist layer in order mitigate dysfunctional feature formation on the wafer 210.

The defect monitoring system 220 is positioned in line or on a fabrication track with respect to the other various processing components involved in the fabrication system 200. That is, the wafer 210 does not need to be taken off-line for defect inspection and then re-aligned in the fabrication system 200 in order for processing of the wafer 210 to resume. In addition, the fabrication system and/or process is not interrupted for the defect inspection to occur.

The defect monitoring system 220 includes a defect measuring system 230 and a defect analyzer 240. Monitoring of the wafer 210 is accomplished in part by measuring for any defects found on the front side surface and back side surface of the wafer 210 using the detect measuring system 230. Examples of the defects may include surface abnormalities, particles, and the like which may obstruct or inhibit subsequent feature formation on the wafer 210. The defect measuring system 230 may comprise any suitable spectroscopic reflectometer, scatterometer, and/or flourescent techniques programmed to detect surface variances at a wide range of wavelengths of light.

Measurements are gathered by the defect measuring system 230 and transformed into usable data by the defect analyzer 240. It should be appreciated that the defect analyzer 240 includes a processor or automated process control (APC) unit. The data may be in the form of values or sets of values which relate and correspond to the defects found on the wafer 210. In addition, such data indicates the quantity and/or quality of these defects. Thus, the data obtained by the monitoring system 220 can be compared to threshold defect limits. The threshold defect limits represent a quantity and/or quality of defects which can be tolerated on the wafer 210 for the duration of the fabrication process and which do not interfere with device performance and/or structure.

When the defects found on the wafer 210 exceed the threshold defect limits, the wafer 210 is transferred to a pre-coat clean module 250 by the monitoring system 220. The pre-coat clean module 250 may include several cleaning techniques which are suitable to clean the front and back sides of the wafer 210 without causing undesirable damage to the wafer 210. An example of a pre-coat cleaning technique is a thermal shock treatment 252 which may be applied to the front and back side surfaces of the wafer 210. The front side of the wafer is cleaned independently from the back side of the wafer.

The monitoring system 220 and the cleaner 250 are coupled in a closed-loop fashion. For example, when the cleaner has substantially removed the defects from the wafer 210, the cleaner 250 transfers the wafer 210 back to the monitoring system 220 in order for the wafer 210 to be examined again for defects. That is, the operations of the defect monitoring system 220 are repeated again to determine whether any defects remain on the wafer 210 as well as to determine the quantity and/or quality of such defects. The cycle between the defect monitoring system 220 and the defect cleaner 250 repeats until the data from the wafer 210 satisfies the threshold defect limits.

Once the water 210 is cleaned to a suitable detect limit, it may proceed to a photoresist coat components 260 wherein a photoresist layer may be formed on the wafer 210. The photoresist layer may be spun on the wafer and then patterned, developed, and hard baked using the appropriate components in order to carry out such processing of the photoresist layer which results in a resist-coated wafer 272. The resist coated wafer 272 may be subjected to a post-coat monitoring system 270 in order to remove any additional defects which may have settled onto the backside of the wafer following the resist coat procedure. The post-coat monitoring system 270 may be a part of the defect monitoring system 220. As such, the post-coat monitoring system 270 includes a defect measuring system 274 which is similar to or the same as the defect measuring system 230.

Because the front side of the wafer 272 has been coated with the photoresist layer, it must be protected during the post-coat inspection. This may be accomplished in part by applying a blanket of nitrogen gas over the front side of the wafer 272. In order to inspect and/or clean the back side without causing undue damage to the front side, the wafer 272 is flipped upside down and held at its edges to allow the back side of the wafer 272 to be cleaned. The back side of the resist-coated wafer 272 may be cleaned by a post-coat back side wafer clean module 280 to an extent such that the back side of the wafer satisfies the threshold defect limit.

Following the post-coat inspection and cleaning, the resist-coated wafer 272 may proceed to post-coat photoresist processing components 290 in order to produce the final device product.

Though not shown in FIG. 2, the system 200 may also include a feed forward control system for feeding the measurements and/or analyzed data forward to subsequent device fabrication systems in order to mitigate early defect formation (e.g., defects formed before resist processing) on future wafers. The feed-forward control system may be coupled to the defect monitoring system 220 and to the device fabrication system 200 and/or to one or more wafer processing components therein. Such arrangement allows for the analyzed data with respect to the current wafer to be used to optimize the fabrication processes of future wafers.

Figure 3:
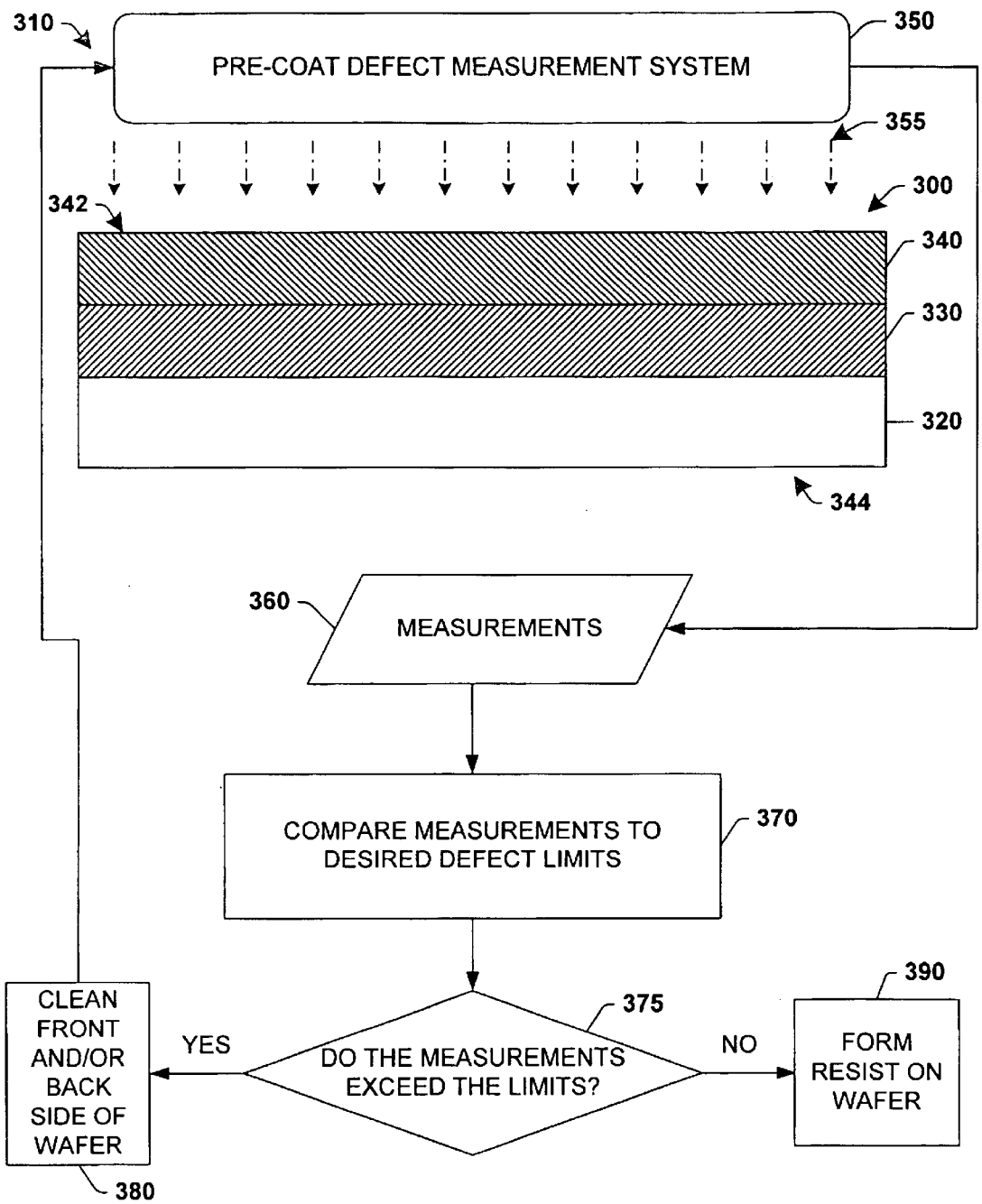
FIG. 3 illustrates a schematic cross-sectional view of a wafer undergoing operations of a schematic flow diagram for an exemplary method of detecting and repairing defects on a wafer before subjecting the wafer to resist processing in accordance with an aspect of the present invention.

Turning now to FIG. 3, a modified flow diagram of a wafer structure 300 undergoing an exemplary method cycle 310 for pre-resist coat defect monitoring according to one aspect of the present invention is depicted. The wafer structure 300 comprises a polycrystalline silicon substrate 320 having one or more layers of material formed thereon. The wafer structure 300 is shown having first 330 and second 340 layers of material formed over the substrate 320. However, it should be appreciated that any number of layers may be formed on the substrate 320. Furthermore, the first 330 and second 340 layers of material may comprise anyone of a metal, nonmetal, organic or inorganic material except neither layer is a photoresist layer.

As can be seen in FIG. 3, the wafer structure 300 is subjected to a cycle of monitoring, measuring, and cleaning when necessary to remove defects from the wafer structure, before the wafer structure can progress to photoresist processing (e.g., initially forming a resist on the wafer). In particular, the wafer structure 300 is monitored for defects on at least one of a front side 342 and a back side 344 surface of the wafer structure 300. When any defects are detected, a defect measurement system 350 measures 355 the defect in terms of a number of the defects found, size of the defects, and/or quality of the defects.

The defect measurement system 350 employs an analyzer and/or processor in order to transform the measurements 360 into usable data in the form of a value or a set of values. These values can be compared (370) to values representing threshold defect limits. Threshold defect limits indicate a quantity and/or quality of defects that the final device product can tolerate in order to fully operational.

If the measured values for defects found on the wafer structure 300 exceed the limit of defects which the wafer structure 300 can tolerate (375), then at least some of the defects found on the wafer structure 300 require removal in order for the wafer structure 300 to proceed to a subsequent processing step. Such removal may be accomplished in part by cleaning (380) the wafer using appropriate techniques so as to not cause further damage to the wafer structure 300.

Once the wafer structure 300 has completed the cleaning process, it is transferred back through the measurement system 350 to be monitored and/or inspected. Any remaining defects on the wafer structure 300 can again be measured in the manner as described above. The cycle of monitoring, measuring, and cleaning the wafer structure repeats until the wafer structure demonstrates that it no longer includes defects beyond the accepted limits for the desired application and intended device product. When the defect measurement system determines that any defects found on the wafer structure are within or below the threshold limits, the wafer structure 300 may proceed to further processing, such as receiving a photoresist layer thereon (390).

The above pre-resist coat inspection and cleaning method 310 of the wafer structure 300 may also be employed after the photoresist layer has been formed as the upper most layer on the wafer structure 300.

As described, the cyclical nature of the method 310 for defect monitoring facilitates distinguishing the origination of defects such as between defects introduced by the water structure 300 and defects introduced later during photoresist processing and/or some other subsequent processing step.

Figure 4:
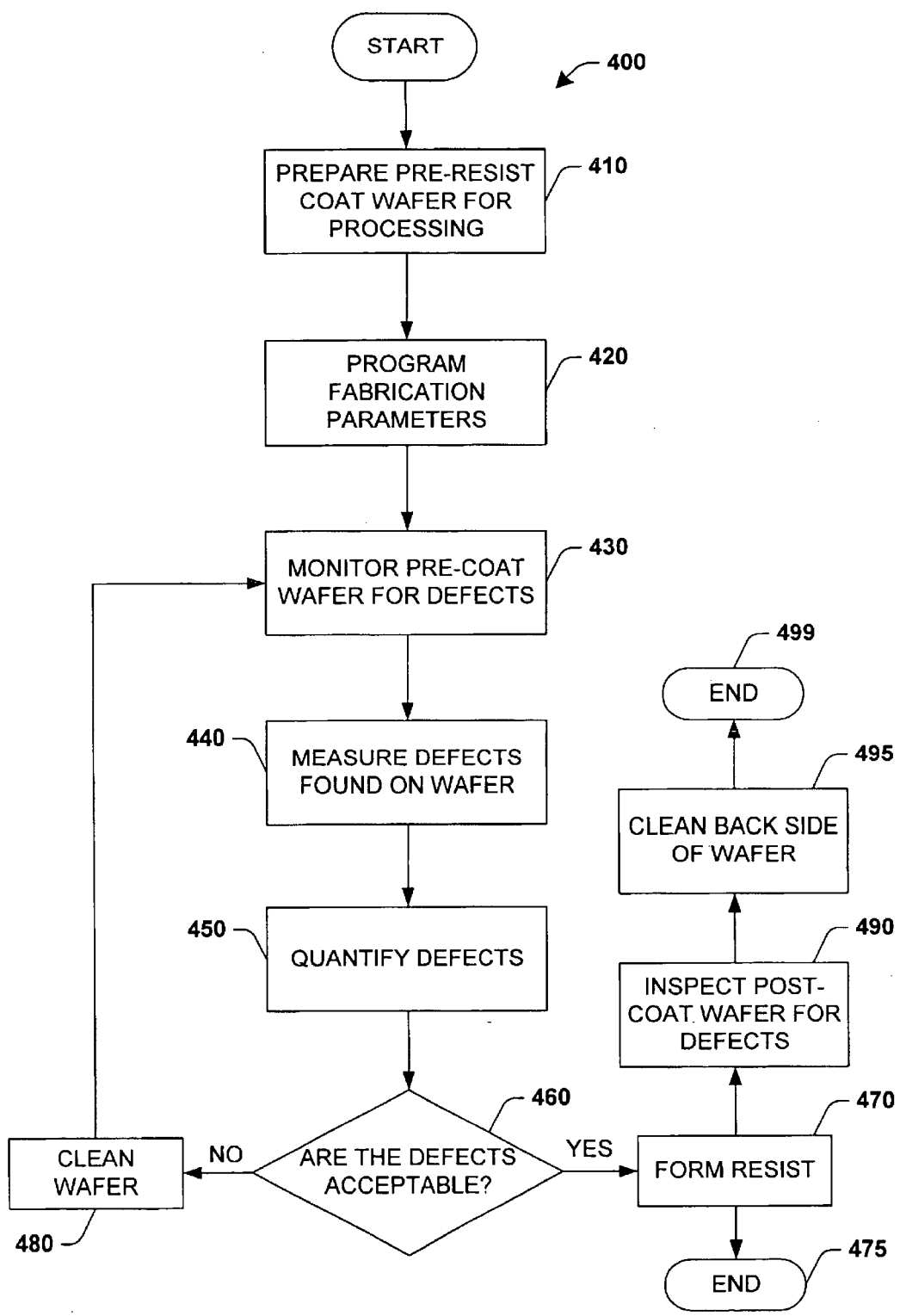
FIG. 4 illustrates a flow diagram of an exemplary method for detecting defects on a wafer structure prior to photoresist processing in accordance with an aspect of the present invention.

Turning now to FIG. 4, a flow diagram of an exemplary method 400 for monitoring a wafer for defects prior to resist processing according to one aspect of the present invention is shown. The method 400 provides a pre-resist coat inspection for defects which have been introduced onto the wafer during preparation of tile wafer (410). Preparation of the wafer may include cleaning and/or smoothing a substrate, forming one or more layers of metal or nonmetal material over the substrate, and general processing of the wafer which is performed just before a photoresist is formed and patterned thereon.

Defects arising from the photoresist processing steps are also possible to form on the wafer. Thus, it is important to distinguish among defects originating from wafer preparation and from photoresist processing in order to mitigate the occurrence of such defects on future wafers. In addition, reducing such defects early on in the device fabrication process (e.g., before photoresist processing begins) decreases the amount of rework or repair needed to remove the defects which may or may not be detected at a later stage of processing. Hence, the present method facilitates increased fabrication efficiency, lower production costs and less waste.

Thus, the method involves preparing a wafer for processing as described above at 410. Next at 420, fabrication parameters may be programmed in order to manufacture the particular device product from the wafer.

The wafer is monitored and/or inspected for defects at 430 by an integrated defect metrology system. Any defects found on the wafer may be measured at 440 by a defect measurement system contained within the integrated metrology system. The defect measurement system obtains data regarding the number of defects, size of defects, and quality of defects found on the wafer at 450. An analyzer also included within the defect metrology system can transform the measurements into usable data. This usable data is in the form of values or sets of values and may be compared to threshold defect limits pre-determined for the particular device product being made.

For example, the device product may have a tolerance level $L_1$ but the measured values may be equivalent to a defect level $L_5$ which far exceeds the given tolerance level. Conversely, the defect level on the wafer may be equal to or less than $L_1$. If the defects on the wafer are within the acceptable limits, then the wafer may proceed to a photoresist processing system at 470, where a photoresist layer may be formed and patterned on the wafer. From there, the wafer continues through the fabrication system and the method 400 ends at 475.

Alternatively, a resist-coated wafer may be inspected further for defects after the resist has been formed and before it has been processed at 490 (e.g. patterned, etched, and the like). In particular, only the back side of the resist-coated wafer may be inspected and cleaned at 495 in order to avoid damaging the resist-coated front side of the wafer. After the resist-coated wafer has been cleaned, it may proceed to subsequent processing steps in order to fabricate the device product. Thus the method may also terminate at 499.

Referring again to the method 400 at 460, comparing the measured values and the acceptable defect limits at 460 determines whether the wafer needs to be cleaned in order to decrease the amount of defects thereon. Thus, if the measured values exceed the threshold limits, the method signals the wafer to be transferred to a wafer cleaning system at 480. Once the cleaning process has been completed, the wafer is returned to the defect metrology system (430) to be monitored for defects again. If any defects are still found, they are measured and method is repeated at 440. Though not shown, the measured values relating to at least one of a quality and/or quantity of defects on the wafer may be fed forward to subsequent fabrication processes in order to mitigate early defect formation in future wafers.

Although the invention has been shown and described with respect to several aspects, it is obvious that equivalent alterations and modifications will occur to others skilled in the art upon the reading and understanding of this specification and the annexed drawings. In particular regard to the various functions performed by the above described components (assemblies, devices, circuits, etc.), the terms (including any reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention.

In addition, while a particular feature of the invention may have been disclosed with respect to only one of several embodiments, such feature may be combined with one or more other features of the other embodiments as may be desired and advantageous for any given or particular application.

What is claimed is:

1. A system for on-track monitoring of defects on a wafer before subjecting the wafer to resist processing comprising:
   a device fabrication system comprising a photoresist coating system and at least one or more wafer processing components for producing a device from a wafer structure;
   a defect metrology system integrated with the device fabrication system operative to inspect at least one of a front side and a back side of the wafer structure for defects and to provide defect information about the wafer structure before it proceeds to the photoresist coating system, the defect metrology system comprising a means for inspecting the back side of the resist-coated wafer structure for defects without adversely affecting the front side of the resist-coated wafer structure; and
   a wafer cleaning system comprising at least one of a pre-resist coat cleaning module and a post-resist coat cleaning module, the system being operatively connected to the defect metrology system for reducing an amount of defects detected on the wafer structure such that after the amount of defects detected thereon are reduced, the wafer structure proceeds to the photoresist coating system component, wherein the wafer cleaning system further comprises a means for cleaning the back side of the resist-coated wafer structure to remove any defects found thereon.

2. The system of claim 1, further comprising a feed forward control system coupled to the defect metrology system and the device fabrication system, wherein the feed forward control system modifies processing components of the device fabrication system in order to mitigate early defect formation which occurs before resist processing for future wafers.

3. The system of claim 1, wherein the defect information about the wafer structure comprises one or more measurements and one or more values corresponding to at least one of a quality or a quantity of defects found on the wafer structure.

4. The system of claim 1, wherein the defect metrology system comprises a measurement system for obtaining data relating to defects found on the wafer structure and an analyzer for performing automated comparisons between the obtained data and acceptable defect requirements.

5. The system of claim 1, wherein the wafer cleaning system is operatively connected to the defect metrology system in a closed loop fashion such that the cleaning system receives the wafer structure to be cleaned and transfers the cleaned wafer structure back to the defect metrology system for inspection.

6. The system of claim 1, wherein the photoresist coating system is coupled to the defect metrology system for forming a photoresist layer on the wafer structure once defects found on the wafer structure have been substantially removed.

7. The system of claim 1, wherein the one or more processing components collectively operate to fabricate and produce the device from the wafer structure.

8. The system of claim 1, wherein the one or more processing components comprise any one of layer deposition components, layer irradiation components, etch components, development components, and polishing components.

9. The system of claim 1, wherein the pre-resist coat and post-resist coat clean modules individually comprise a thermal shock treatment.

10. The system of claim 1, wherein the defect metrology system comprises an artificial intelligence component such that the wafer is cleaned when defects are detected thereon.

11. A method for on-track monitoring of defects on a wafer before subjecting the wafer to resist processing comprising:
    introducing a pre-resist coat wafer structure into a device fabrication system in order to yield a device product, the wafer structure having a front side and back side;
    monitoring at least one of the front side and the back side of the wafer structure for defects before a photoresist layer is formed on the wafer structure;
    measuring the defects found on the wafer structure in order to obtain defect information relating to the defects found on the wafer structure:
    comparing the defect information with threshold defect limits; and cleaning at least one of the front side and the back side of the wafer structure to reduce the defects found on that side of the wafer structure prior to forming a photoresist layer over the front side of the wafer structure, wherein cleaning the front side of the wafer is performed independently of cleaning the back side of the wafer.

12. The method of claim 11, wherein the defect information comprises one or more measurements and one or more values corresponding to at least one of a quality or a quantity of defects found on the wafer structure.

13. The method of claim 11, wherein measuring the defects found on the wafer structure is performed by a defect metrology system, the metrology system comprising a measurement system for obtaining data relating to defects found on the wafer structure and an analyzer for performing automated comparisons between the defect information and threshold defect limits, the analyzer comprising an automated process control unit for closed-loop operation between measuring the wafer for defects and cleaning the wafer.

14. The method of claim 11, further comprising:
    forming a photoresist layer over the front side of the wafer structure, wherein the wafer structure does not contain defects over the threshold defect limits to form a resist-coated wafer structure;
    inspecting the back side of the resist-coated wafer structure for defects without adversely affecting the front side of the resist-coated wafer structure; and
    cleaning the back side of the resist-coated wafer structure to remove any defects found thereon.

15. The method of claim 14, wherein cleaning the back side of the resist-coated wafer structure comprises:
    covering the front side of the resist-coated wafer structure with nitrogen gas;
    rotating the wafer structure such that the back side of the resist-coated wafer structure may undergo a thermal shock treatment in such a way that the wafer structure is held at its edges so as to not adversely affect the front side of the resist-coated wafer structure.

16. The method of claim 11, wherein the device fabrication system comprises one or more processing components to collectively fabricate and produce the device from the wafer structure.

17. The method of claim 16, wherein the one or more processing components comprise any one of layer deposition components, layer irradiation components, etch components, development components, hard-bake components and polishing components.

18. The method of claim 11, wherein cleaning the front side of the wafer is performed by using a thermal shock treatment.

19. The method of claim 11, wherein cleaning the back side of the wafer is performed by using a thermal shock treatment.

20. The method of claim 11, further comprising feeding the obtained defect information forward to a subsequent fabrication process in order to mitigate defect formation on future pre-resist coat wafers.

21. An online method for real-time pre-resist coat and post-resist coat inspection of a wafer for defects comprising:

providing a pre-resist coat wafer structure, the wafer structure having a front side surface and a back side surface;

inspecting at least one of the front side surface and the back side surface of the pre-resist coat wafer structure for defects;

measuring the defects found on the pre-resist coat wafer structure in order to obtain defect information relating to the defects found on the wafer structure;

cleaning at least one of the front side and the back side of the wafer structure to reduce the defects found on that side of the pre-resist coat wafer structure when the measured defects on that side are greater than me threshold defect limits;

forming a photoresist layer over the front side of the pre-resist coat wafer structure to create a resist-coated wafer structure;

inspecting the back side of the resist-coated wafer structure for defects without adversely affecting the front side of the resist-coated wafer structure;

cleaning the back side of the resist-coated wafer structure to remove any defects found thereon; and patterning the resist-coated wafer structure to thereby form one or more features in the wafer structure.

* * * * *